United States Patent [19]
Effenberger et al.

[11] Patent Number: 5,315,008
[45] Date of Patent: May 24, 1994

[54] PROCESS FOR THE PREPARATION OF ISOTHIAZOLONE

[75] Inventors: Reinhard Effenberger; Leonard Shorr, both of Haifa; Yehuda Keren, Kiryat Motzkin, all of Israel

[73] Assignee: Bromine Compounds Ltd., Beer-Sheva, Israel

[21] Appl. No.: 831,465

[22] Filed: Feb. 5, 1992

[30] Foreign Application Priority Data

Feb. 6, 1991 [IL] Israel ............ 97166

[51] Int. Cl.⁵ ............... C07D 91/10
[52] U.S. Cl. ................. 548/182
[58] Field of Search ............ 548/182

[56] References Cited

U.S. PATENT DOCUMENTS

3,761,488  9/1973  Lewis et al. ............ 260/302
3,849,430  11/1974  Lewis et al. ............ 260/302 A Primary Examiner—Marianne M. Cintins
Assistant Examiner—Catherine Scalzo
Attorney, Agent, or Firm—Michael N. Meller

[57] ABSTRACT

Mixtures of 2-methyl-isothiazolin-3-one (5H-MIT) and 5-chloro-2-methylisothiazolin-3-one (5Cl-MIT), are prepared by the chlorination of N-methyl-3-mercapto-propionamide (MMPA) with chlorine in a halogenated solvent in continuous operation.

27 Claims, 11 Drawing Sheets

PROCESS FOR THE PREPARATION OF ISOTHIAZOLONE

FIELD OF THE INVENTION

This invention relates to the preparation of isothiazolone derivatives, and, more specifically, to the preparation of 2-methyl-isothiazolin-3-one and its mixtures, in various proportions, with 5-chloro-2-methylisothiazolin-3-one. Said mixtures are designated by the abbreviation MIT, the non-chlorinated component being designated by 5H-MIT, and the chlorinated component as 5Cl-MIT. MIT is a biocidal product and is effective for the control of microorganisms.

BACKGROUND OF THE INVENTION

U.S. Pat. No. 3,761,488 describes and claims a class of isothiazolone compounds, which comprises both components of MIT.

U.S. Pat. No. 3,849,430 describes and claims a process for preparing the said compounds by halogenation, accompanied by cyclization, of disulfideamides or mercaptoamides.

U.S. Pat. No. 4,105,431 discloses and claims the same compounds as compositions for inhibiting the growth of bacteria, fungi or algae, and a method for inhibiting said growth by the use of said compounds. EP 95907 claims a biocidal composition containing 3-isothiazolones, which is characterized in that the impurity content in the composition of nitrosamines plus nitrosamine precursors is less than 15 ppm of the 3-isothiazolones.

EP 363011 claims microbiocidal compositions of MIT in which the percentage of 5Cl-MIT is from 1.2 to 25.4%, the remaining part of the composition being 5H-MIT. Increased biological activity over that of each material separately is stated to be possessed by the compositions, which are also said to produce less skin-sensitization than compositions containing higher amounts of 5Cl-MIT. The compositions are prepared by semi-batch reaction between N-methyl-3-mercaptopropionamide (MMPA) and $Cl_2$ in monochlorobenzene, the molar ratio of $Cl_2$ to MMPA being 2.

EP 375265 claims a process for the preparation of crystalline isothiazolone monohydrochloride salts by chlorination of disulfidediamides or mercaptoamides, to give a crude product which is purified by crystallizing from chlorobenzene via reduction of the HCl content.

All the processes described in the literature, and in particular in the aforementioned patents, are batch or semi-batch. One of the advantages of MIT as an industrial biocide is that it rapidly decomposes in the environment and therefore does not constitute an ecological hazard. On the other hand, its shelf-life and that of its formulations can be seriously shortened by even traces of destabilizing impurities. Furthermore, the chemistry involved in MIT manufacture is multi-step and very complex. The composition of the product, the level of impurities and, as a result, the stability of formulations containing MIT, can be radically affected by even minor process fluctuations. For this reason, batch or semi-batch operations have been found to produce products of variable and inferior quality.

In addition, and in spite of the advantages claimed for MIT compositions in which the 5Cl component is in the minority, as in EP 363011, the most useful compositions are those in which the 5Cl/5H ratio is 2.5 or higher. Batch and semi-batch operations directed to produce mixtures of the said high 5Cl/5H ratios have the disadvantage of causing a large loss of yield because of the formation of large amounts of overchlorinated materials (mainly 4,5-dichloro-MIT).

It is a purpose of this invention to provide a process for the manufacture of MIT mixtures that will be free of the drawbacks of known processes, and will afford high yields.

It is another purpose of the invention to provide such a process which will permit to manufacture MIT mixtures in which the chlorinated and unchlorinated component are present in any desired molar ratio, without loss of yield to undesired by-products.

It is a further purpose of the invention to provide such a process which will permit preparation of MIT mixtures in which the 5Cl-5H ratio is greater than 2.5, and which do not cause large losses of yield due to the production of overchlorinated materials.

It is a still further purpose of the invention to provide such a process which will yield solid MIT product as its white HCl-salt (MIT.HCl) which is adequately stable at temperatures convenient for shipping in such a form.

It is a still further purpose of the invention to provide such a process that can be carried out efficiently and with high yields by means of the same apparatus, no matter what the desired ratio of the components of the MIT mixture may be.

Other purposes and advantages of the invention will appear as the description proceeds.

SUMMARY OF THE INVENTION

The process according to the invention is essentially characterized in that it comprises chlorination of N-methyl-3-mercaptopropionamide (MMPA) with chlorine in an halogenated solvent in continuous operation.

The chlorination is preferably carried out by contacting a concentrated solution of MMPA in a chlorinated solvent with gaseous chlorine or with a solution of chlorine in the same solvent. Desirable concentrations of the MMPA solution are between 50 and 80%. Preferably, the flow of the solvent in the reactor is set as to obtain a holdup time (hereinafter briefly designated by HUT) in the range of 0.1 to 30 minutes, preferably 0.5 to 7 minutes, and still more preferably, 1 to 3 minutes; the MMPA flow rate is chosen so that the concentration of MMPA in the reaction mixture is in the range of 1 to 20%, preferably 2 to 10%; the chlorine flow rate is set so as to obtain a $Cl_2$-MMPA molar ratio comprised between 1.5 and 4.0, preferably 2.0 and 3.2; and the reaction temperature is maintained in the range of 15° to 50° C., preferably 20° to 40° C., and still more preferably, 25° to 35° C.

In a preferred form of the invention, the reaction is carried out in two stages: in the first stage the MMPA is contacted with chlorine under the conditions hereinbefore set forth and under stirring, in a first reactor, thereafter the reaction mixture is transferred to a second reactor and the reaction is allowed to continue under stirring and under degassing for a time greater than 2 minutes and preferably greater than 10 minutes. The degassing is preferably carried out to such an extent as to reduce the chlorine content of the solvent to less than 1 mole, preferably less than 0.1 mole, per mole of products, by the time the reaction mixture leaves said second reactor.

The HUT in the first reactor which is optimum for the production of that 5Cl/5H ratio which is desired in the product will depend on the other chlorination conditions, the reactor geometry and the manner in which the Cl$_2$ is introduced. Limited experimental adjustments suffice to establish the optimum operating conditions.

DETAILED DESCRIPTION OF PREFERRED EMBODIMENTS

Since the reaction between chlorine and MMPA is very exothermic (ca. 1000 kcal/kg MMPA converted completely to 5Cl-MIT) it is convenient and desirable to pre-cool the solvent and the chlorine before their entry into the reactor in order to facilitate removal of the reaction heat in an efficient manner. To maintain the preferred reaction temperatures, suitable cooling should be employed, preferably external cooling both in a solvent cooling unit and in the reactor itself.

The use of concentrated MMPA solutions enables easily to carry out changes in the MMPA reactor concentration; whereby to control as desired the 5Cl/5H ratio of the resulting MIT product.

Examples of chlorinated solvents suitable for carrying out the invention are: benzene, toluene, chlorobenzene, dichloromethane, 1,2-dichloroethane, perchloroethylene and chloroform, but other halogenated aliphatic or aromatic solvents can be used.

In order to maintain the HUT in the first reactor within the preferred range, to avoid the formation of overchlorinated products, it is preferred—as has been set forth—to transfer the reaction mixture, which contains a certain amount of intermediates which have not yet been fully converted into the desired product, to a second stirred vessel in which the reaction proceeds and in which the HUT of the reaction mixture is greater than 2 minutes, and preferably greater than 10 minutes. In this second reactor, intermediates convert to final products and overchlorination is prevented by degassing, preferably by means of an air blast passed through the stirred mixture, in order to reduce the chlorine content of the solvent to less than 1 mole per mole of products, preferably less than 0.1 mole per mole of products. Although the main reason for degassing in the continuous process is to remove Cl$_2$, the air blast in said second reactor also removes excess HCl which removal lowers the product solubility, and produces a filterable slurry of MIT-HCl salt. Removal of HCl actually happens far more readily than that of Cl$_2$, because of the much lower solubility of the former gas in organic solvents (for example, see W. F. Linke (American Cyanamid Co.), 'Solubilities', Van Nostrand, N.Y. (1958), pp. 786, 1118–solubilities of HCl and Cl$_2$ in 1000 ml. CCl$_4$ at 20° C. are 6.2 g and 147 g respectively).

The HUT in the second reactor beyond 10 minutes will largely depend upon whether the subsequent filtration step is performed in a continuous, semi-batch or batch operation. The choice between these depends on engineering considerations and on the equipment available. In any case, the HUT in the second reactor will be controlled by the concentration level of the reaction intermediate by GC, as shown in Example 3.

The concentration of intermediate is greatest at the reactor exit and decreases as the reaction mixture is passed through the second reactor. Decrease in the concentration of this material is accompanied by an increase in the concentration of (mainly) 5Cl-MIT. The time required for complete disappearance of this material depends on several factors, in particular the HUT in the first reactor, since increasing this HUT will, naturally, decrease the amount of intermediate present at the exit point. However, the reactor HUT cannot usually be increased enough so that intermediates have time to convert into final products, because the presence of the excess Cl$_2$ causes further conversion of the desired product into unwanted overchlorinated by-product. The use of a second reactor, in which the excess Cl$_2$ is removed (by air or nitrogen blast) enables conversion of intermediate to product without the accompanying problem of overchlorination. The slurried product is maintained in the second reactor at least until the disappearance of this reaction intermediate.

The second reactor can therefore be operated in continuous fashion, if the filtration is suitable for such a format, and in this case the flow rate of the reaction mixture will be controlled so as to obtain the desired HUT. Since there is no upper limit to the HUT in this reactor, two secondary reactors can be used in alternating fashion to supply a batch filtration system. Before filtration, the slurry is preferably cooled to maximize the precipitation of MIT-HCl salt.

The continuous operation of the first, or main, reactor is the critical factor in maintaining product quality. This procedure enables (i) production of stable, intermediate-free MIT, (ii) good control over the 5Cl/5H MIT ratios in the product, and (iii) subsequent precipitation of the MIT as the HCl salt with high purity (>98 GLC area %). The filtered MIT-HCl cake is washed with fresh solvent and the washed cake, containing 30–60% residual wash solvent, can either be vacuum-dried to give solid MIT as its HCl salt (a mixture of 5H and 5Cl-MIT-HCl) or dissolved from the filter with cold water to give, finally, an aqueous MIT formulation.

The applicant has determined that the solid MIT HCl salt is stable and does not decompose exothermically over the range 20°–180° C. It has also been found that MIT-HCl produced by the process according to the invention is stable at <10° C. for at least two years. This solid product can be shipped as is, or, in the case that an aqueous formulation is the desired end product, the solid MIT-HCl salt can be dissolved in cold water. This dissolution can be carried out either on the dry MIT cake or on the solvent wet cake on the filter. In the latter case, the two-phase solution is first taken to a separator, where the solvent phase is separated and returned to the second stirred reactor to recover dissolved MIT. It has been found that the solubility of, in particular, 5Cl-MIT (which is not bound to HCl, as occurs on dissolution of MIT-HCl in water) in organic solvents can be quite high (>=10% for most chlorinated solvents). The recycle of this solvent containing dissolved MIT to the second reactor is an important feature of the process, for attempts to dispose of it or isolate the MIT therefrom are costly operations, which can be dangerous in view of the nature of the materials involved.

The solubility of 5Cl-MIT is lowest in toluene, moderate in chlorobenzene and highest in solvents like chloroform, dichloromethane or dichloroethane. For this reason, and because toluene is not the optimum solvent, being reactive under the reaction conditions used and being converted into chlorotoluenes, lachrymatory substances and diphenylethanes, chlorobenzene is the preferred solvent for carrying out the process according to the invention.

The aqueous phase is then brought to the desired pH and stabilized by methodology already known (see, for example, EP 0 300 483-examples 1, 2 and EP 0 095 907-example 2). The resulting solution is diluted with water to give the desired final active ingredients (AI) concentration.

The filtrate and washings from the MIT-HCl cake filtration step are combined. This combined solvent contains up to 0.5–5% dissolved organics. In addition to the usual products and by-products present (a partial listing of identified materials is given below), decomposed materials are probably also present. It has been found that contamination of the solid MIT-HCl with such filtrate decreases the stability of the solid. It is therefore desirable to remove at least the filtrate contaminants responsible for destabilization of the solid before attempting to recycle the filtrate for reuse. It has been found that suitable treatment (hereafter called regeneration) of the used solvent, which enables its reuse in the process, can be either by distillation, or washing with aqueous base, water and aqueous HCl, or passing the solvent over an absorbent such as active charcoal, silica gel, diatomaceous earth, etc. In the case where an aqueous wash is used for the regeneration, the water concentration in the solvent must be reduced to <1000 ppm, preferably <300 ppm, otherwise an inferior MIT-HCl product will result. The drying can be carried out by distillation of a small fraction of the solvent (removal of water as an azeotrope) or by passing the washed solvent over silica gel beads, or by other means known in the art. The solvent can also be recycled without any regeneration, but in most cases, serious loss of product occurs after 3–5 such (untreated) recycles.

By operating as described herein, MMPA is completely converted to a mixture of products consisting mainly of 5H-MIT and 5Cl-MIT, (up to 90% yield, 5Cl/5H ratio 0.1–10.0).

During the reaction of MMPA to form 5H-MIT and 5Cl-MIT, several by-products are formed:

(i) N-methyl 3-chloropropionamide (BETA);
(ii) 4,5-dichloro-2-methylisothiazolin-3-one (4,5-dichloro-MIT);
(iii) 4,4,5,5-tetrachloro-2-methylisothiazolidin-3-one;
(iv) 4,4,5-trichloro-2-methylisothiazolin-3-one.
(v) Several other compounds have been tentatively identified by GC-MS analysis of the reaction solvent. Among these are N-methyl dichloropropenamide, N-methyl dichloropropionamide, isothiazolin-3-one and 4,5-dichloro-2-methylisothiazolin-3-one-1-oxide.

These by-products are found in the reaction solvent and in the wash solvent. The solid MIT product obtained after filtration/washing sometimes contains ca. 0.5–1.0% each of BETA and 4,5-dichloro-MIT. Other by-products may be present also but in amounts not exceeding 0.5% in any individual case.

The by-products BETA and 4,5-dichloro-MIT are not present in the final formulated product in amounts exceeding 0.1%.

The dry solid MIT-HCl salt has the following composition:

| | |
|---|---|
| (i) 5-chloro-2-methylisothiazolin-3-one.HCl salt | 9–90% |
| (ii) 2-methylisothiazolin-3-one.HCl salt | 90–9% |
| (iii) N-methyl 3-chloropropionamide | <=1% |

-continued

| | |
|---|---|
| (iv) 4,5-dichloro-2-methylisothiazolin-3-one | <=1% |

The invention will be further illustrated by the description of the following, non-limitative examples.

EXAMPLE 1—Semi-Batch Operation

This example shows the difficulty of overcoming high conversion of MMPA to (undesired) by-product (4,5-dichloro-MIT) when an MIT mixture with a 5Cl/5H ratio of >=2.5 is desired.

To a stirred reactor containing 5 parts of 1,2-dichloroethane (EDC) were simultaneously added 23 parts of an MMPA solution in EDC ([MMPA]=0.44 g/ml) and 21 parts of $Cl_2$ gas over 70 minutes. This gave a $Cl_2$/MMPA mole ratio of 3.5. The reaction temperature was maintained at 18° C. On completion of this addition, a sample of the reaction mixture was examined by GLC and was shown to contain (area %) 7.5% BETA, 8.1% 5H-MIT, 16.2% 5Cl-MIT and 50.7% 4,5-dichloro-MIT. Some 16% of other materials were also present. The 5Cl/5H ratio was 2 for a total MIT content (5H+5Cl) of 24.3%.

On repeating this reaction, but using a $Cl_2$/MMPA mole ratio of 3.2, the reaction mixture contained 10.6% BETA, 18.8% 5H-MIT, 39.1% 5Cl-MIT and 26.2% 4,5-dichloro-MIT. The 5Cl/5H ratio was 2.1 for a total MIT content (5H+5Cl) of 57.9%.

The reaction was again repeated with reduction of the $Cl_2$/MMPA mole ratio to 2.7. The reaction mixture contained 13.8% BETA, 21.9% 5H-MIT, 47.0% 5Cl-MIT and 13.8% 4,5-dichloro-MIT. The 5Cl/5H ratio was 2.2 for a total MIT content (5H+5Cl) of 68.9%.

This example shows that, under semi-batch operation, a good 5Cl/5H ratio cannot be achieved if the total MIT content is to be in excess of 69%.

EXAMPLE 2

The reaction system consisted of a 100 mL glass first reactor, a 2000 mL glass second reactor and a glass sinter filter. EDC, gaseous $Cl_2$ and 80% MMPA in EDC were separately fed into the first reactor at rates of 67 mL/min, 7–9 g/min and 5 mL/min, respectively. This reactor was stirred and cooled in an ice bath and the EDC line was also cooled so as to maintain a reaction temperature of 20° C. The HUT in this reactor was 1.3 min. The exiting reaction mixture was then fed into the second reactor, also stirred but not cooled, and a blast of $N_2$ (1 L/min) was passed through the stirred reaction mixture. The temperature in this reactor was 25° C. and the HUT was 9 min. On exiting the reactor, the slurry was sampled and analysed by GC to determine its composition, and then fed into the sinter (for isolation of solid product by filtration).

Using the continuous reaction system described above, two experiments were carried out.

(i) The $Cl_2$/MMPA mole ratio was 3.4. The product mixture exiting the second reactor had a composition of 6.6% BETA, 18.8% 5H-MIT, 48.5% 5Cl-MIT, and 23.0% 4,5-dichloro-MIT. The 5Cl/5H ratio was 2.6 for a total MIT content (5H+5Cl) of 67.3%.

(ii) The $Cl_2$/MMPA mole ratio was 2.9. The reaction mixture contained, after passing through the second stirred reactor, 8.6% BETA, 19.7% 5H-MIT, 66.7% 5Cl-MIT and 5.0% 4,5-dichloro-MIT. The 5Cl/5H ratio was 3.4 for a total MIT content (5H+5Cl) of 86.4%.

This example therefore proves that a good 5Cl/5H ratio can be achieved for total MIT contents in excess of 69%, and higher even than 86%. At equivalent reagent feed ratios, the continuous process provides yields of total MIT 25% and more, greater than those of the semi-batch operation in Example 1.

EXAMPLE 3

This example shows the necessity for maintaining the reaction mixture exiting the reactor for a certain period in a second stirred reactor in order to enable conversion of intermediate(s). Without such a second reactor, the solid MIT-HCl obtained on filtration of the reaction mixture exiting the degasser contains intermediate(s) and produces a product which discolorizes on storage.

At least one of these intermediates can be readily observed by GLC, eluting just after 5Cl-MIT (ca. 0.2 min later). The GLC conditions used for observation of this intermediate were: Hewlett-Packard Model HP 5890 fitted with a 4 m capillary column (HP series 530 micron) containing methyl silicone as liquid phase and $N_2$ as carrier gas. The operating conditions were: (a) initial temperature/time=90° C./2 min; (b) rate of temperature increase =20° C./min; (c) final temperature/time=250° C./4 min. Under these conditions the retention times of the components were: BETA 1.2 min, 5H 1.5 min, 5Cl 2.2 min, intermediate 2.4 min, and 4,5-dichloro 3.8 min.

A solution of MMPA (0.06 g/ml) in DCM was fed into the reactor together with $Cl_2$ so that the $Cl_2$/MMPA mole ratio was 3.1. The reactor hold-up time was 0.5 or 2.5 minutes and its temperature 26° C. The product exiting the reactor was either (i) filtered immediately or (ii) kept in a second stirred reactor at ca. 30° C. for 8 or 12 minutes while blasting air through the stirred mixture. After these hold-up times in the second reactor, the solids were filtered and examined. The results are shown below.

TABLE I

| Reactor 1 HUT | Reactor 2 HUT | % Intermediate in Mixture | 5Cl/5H in Solid | Color of Filtered Solid |
|---|---|---|---|---|
| 0.5 | 0.0 | 37.0 | 2.26 | red-purple |
| 0.5 | 8.0 | 12.1 | 2.85 | red-orange |
| 0.5 | 12.0 | 0.0 | 3.61 | off-white |
| 2.5 | 0.0 | 14.3 | 2.45 | reddish |
| 2.5 | 11.0 | 0.0 | 2.98 | white |

EXAMPLE 4

This shows the necessity of degassing the reaction mixture which exits the reactor in order to "freeze" its composition. Degassing, which removes excess $Cl_2$ from the exiting reaction mixture, prevents continuation of the chlorination after the reactor and stops excessive formation of 4,5-dichloro-MIT, an undesired by-product.

A solution of MMPA in dichloromethane (DCM, [MMPA]=1.2 g/ml) and gaseous $Cl_2$ were fed into the reactor. The $Cl_2$/MMPA mole ratio was 3.0 and the reaction temperature was 20° C. The reactor had a holdup time of one minute and the exiting reaction mixture was fed directly to the second stirred reactor through which no air was passed. The product mixture exiting the second stirred reactor had a composition of 5.7% BETA, 22.3% 5H-MIT, 48.6% 5Cl-MIT and 19.9% 4,5-dichloro-MIT. The 5Cl/5H ratio was 2.2.

The run was now repeated by passing a stream of air through the second reactor for removal of excess $Cl_2$. The product mixture exiting the second stirred reactor had a composition of 4.2% BETA, 26.2% 5H-MIT, 62.3% 5Cl-MIT and 6.6% 4,5-dichloro-MIT. The 5Cl/5H ratio was 2.4.

EXAMPLE 5

This example demonstrates the range of 5Cl/5H ratios accessible by changes of the $Cl_2$/MMPA mole ratio, the MMPA concentration in the reactor, the reactor hold-up time and the reactor temperature. The runs were carried out by contacting a solution of MMPA in EDC ([MMPA]=0.12 g/ml) or monochlorobenzene (MCB, [MMPA]=0.06 g/ml or 0.03 g/ml) with $Cl_2$ in a cooled, stirred reactor followed by degassing the exiting product stream with air in a second stirred reactor. The $Cl_2$/MMPA mole ratio was 1.8-3.5, the reactor hold-up time (HUT) ranged from a low of 0.7 minutes to a high of 5 minutes, and the reactor temperature was in the range of 25°-45° C.

TABLE II

| $Cl_2$/MMPA | °C. | HUT | BETA | 5H-MIT | 5Cl-MIT | 4,5-dichloro-MIT | 5Cl/5H |
|---|---|---|---|---|---|---|---|
| SET I: In EDC; [MMPA] = 0.12 g/ml | | | | | | | |
| 1.8 | 45 | 1.0 | 15.2 | 62.5 | 8.9 | <0.5 | 0.14 |
| 2.2 | 25 | 0.7 | 6.6 | 60.5 | 29.1 | 3.0 | 0.48 |
| 2.7 | 30 | 2.5 | 1.2 | 31.8 | 56.4 | 2.1 | 1.77 |
| 2.9 | 25 | 2.5 | 8.6 | 19.7 | 66.7 | 5.0 | 3.39 |
| 3.2 | 30 | 1.2 | 5.3 | 17.2 | 65.5 | 11.2 | 3.81 |
| 3.5 | 30 | 2.0 | 5.1 | 18.2 | 50.4 | 21.0 | 2.77 |
| SET II: In MCB; [MMPA] = 0.06 g/ml | | | | | | | |
| 2.6 | 25 | 5.0 | 7.7 | 25.4 | 62.5 | 1.9 | 2.46 |
| 2.9 | 25 | 7.0 | 8.3 | 19.4 | 58.2 | 8.1 | 3.00 |
| 3.0 | 35 | 1.0 | 7.5 | 8.2 | 70.9 | 8.2 | 8.65 |
| SET III: In MCB; [MMPA] = 0.03 g/ml | | | | | | | |
| 3.0 | 37 | 2.4 | 8.0 | 10.3 | 71.6 | 7.4 | 6.95 |
| 3.5 | 25 | 1.0 | 8.3 | 6.9 | 70.9 | 10.3 | 10.27 |

EXAMPLE 6

This example shows the effect of varying the reactor hold-up time on the composition of the product mixture. The runs were carried out using DCM solution of MMPA ([MMPA]=0.12 g/ml), a $Cl_2$/MMPA mole ratio of 2.9-3.0, a reaction temperature of 25° C., a second stirred reactor held at a temperature of 27°-30° C. and a $N_2$ stream for degassing.

TABLE III

| HOLD-UP TIME | BETA | 5H-MIT | 5Cl-MIT | 4,5-dichloro-MIT | 5Cl/5H |
| --- | --- | --- | --- | --- | --- |
| 1 | 8.7 | 41.1 | 47.4 | 1.6 | 1.15 |
| 3 | 6.0 | 25.2 | 61.9 | 4.4 | 2.45 |
| 5 | 6.2 | 21.7 | 62.9 | 7.4 | 2.89 |
| 13 | 6.7 | 19.0 | 57.1 | 14.7 | 3.01 |

EXAMPLE 7

This example shows the effect of using solvent wet with water on the MIT reaction.

These runs were carried out using an MMPA concentration—in MCB-of 0.02 g/ml, a $Cl_2$/MMPA mole ratio of 2.9–3.1, a reaction temperature of 25° C. and hold-up time of one minute, a second stirred reactor held at a temperature of 27°–30° C. and an air stream for degassing. The MCB contained 300 ppm or 1000 ppm water.

For MCB containing 300 ppm water, the solid product mixture (after filtration) contained 1.1% BETA, 19.2% 5H-MIT and 77.7% 5Cl-MIT.

When the MCB containing 1000 ppm water was used, the solid product was sticky and contained, in addition to 2.5% BETA, 14.3% 5H-MIT and 60.6% 5Cl-MIT, at least two other (unidentified) compounds accounting for a total of 16%.

EXAMPLE 8

This example shows the effect of diluting the MMPA feedstock solution on the composition of the reaction mixture. Dilution of the MMPA feedstock enables better selectivity to MIT-HCl and an improved 5Cl/5H ratio. These runs were carried out using MMPA concentrations in DCM or MCB of 0.12 or 0.06 g/ml, a $Cl_2$/MMPA mole ratio of 2.9–3.1, a reaction temperature of 25° C., a second stirred reactor held at a temperature of 27°–30° C. and an air stream for degassing.

TABLE IV

| [MMPA] | SOLVENT | BETA | 5H-MIT | 5Cl-MIT | 4,5-dichloro-MIT | 5Cl/5H |
| --- | --- | --- | --- | --- | --- | --- |
| 0.12 | DCM | 5.3 | 28.7 | 53.7 | 4.8 | 1.87 |
| 0.06 | DCM | 4.3 | 24.0 | 64.0 | 2.7 | 2.67 |
| 0.12 | MCB | 8.7 | 24.4 | 60.3 | 4.3 | 2.47 |
| 0.06 | MCB | 8.4 | 20.0 | 63.8 | 5.7 | 3.19 |

EXAMPLE 9

This example shows the effect of varying the type of solvent (DCM, MCB or toluene (T)) on the composition of the solid MIT-HCl which precipitates from the reaction mixture (slurry) after degassing. The differences observed stem mainly from the different solubility of the 5Cl-MIT-HCl component in the said solvent. These runs were carried out using an MMPA concentration in the solvent of 0.06 g/ml, a $Cl_2$/MMPA mole ratio of 2.9–3.1, a reaction temperature of 25° C., a second stirred reactor held at a temperature of 27°–30° C. and an air stream for degassing.

TABLE V

| SOLVENT | SAMPLE | BETA | 5H-MIT | 5Cl-MIT | 4,5-dichloro-MIT | 5Cl/5H |
| --- | --- | --- | --- | --- | --- | --- |
| DCM | SLURRY | 3.0 | 14.9 | 76.0 | 1.4 | 5.10 |
|  | SOLID | 1.0 | 20.8 | 60.1 | 0.0 | 2.89 |
| MCB | SLURRY | 8.3 | 19.4 | 58.2 | 8.1 | 3.00 |
|  | SOLID | 1.8 | 24.9 | 71.4 | 0.6 | 2.89 |
| T | SLURRY | 7.3 | 16.1 | 66.0 | 2.2 | 4.10 |
|  | SOLID | 1.7 | 20.8 | 72.9 | 0.0 | 3.51 |

EXAMPLE 10

The solid MIT-HCl cakes, wet with 40–60% of solvent, can be dissolved in water in order to produce aqueous formulations. The organic solvent is removed by phase separation. On addition of water, the MIT-HCl salt is decomposed into the free MIT and HCl dissolved (H-bonded) to water. The free MIT, particularly the 5Cl-MIT component, is very soluble in organic solvents (in contrast to the less soluble 5Cl-MIT-HCl salt) and considerable loss of this component can occur via its extraction into the organic phase which separates during the dissolution of the MIT-HCl cake in water.

This example shows the relative loss of 5Cl-MIT into the organic phase on solution of the cake in water. The solvents used in the reaction for the preparation of the MIT-HCl wet cake were DCM, MCB and T. The cakes were dissolved in an amount of water such that the volumes of water and organic phase obtained were equal. The phases were separated and analyzed by GLC. Figures are given as percent of total component present in each phase.

TABLE VI

| SOLVENT | PHASE | BETA | 5H-MIT | 5Cl-MIT | 4,5-dichloro-MIT |
| --- | --- | --- | --- | --- | --- |
| T | ORG. | 5.7 | 2.9 | 46.9 | 84.8 |
|  | AQ. | 94.3 | 97.1 | 53.1 | 15.2 |
| MCB | ORG. | 10.3 | 6.5 | 67.2 | 90.9 |
|  | AQ. | 89.7 | 93.5 | 32.8 | 9.1 |
| DCM | ORG. | 40.0 | 33.5 | 90.6 | 97.0 |
|  | AQ. | 60.0 | 66.6 | 9.4 | 3.0 |

These results clearly show that loss of the desired 5Cl-MIT component into the organic phase is least in toluene and greatest in dichloromethane, with monochlorobenzene in the middle. Toluene also undergoes some chlorination (and diphenylethane formation) during the reaction and DCM is difficult to recover because of its high volatility. These results indicate that MCB is the preferred solvent for performing the reaction as described in the above examples.

EXAMPLE 11

This example shows that the continuous reaction can be carried out over an extended period in MCB with recycle of the solvent after filtration to remove the solid MIT-HCl wet cake. In this run, a solution of MMPA in MCB was fed into a stirred 500 ml jacketed reactor, together with a solution of chlorine in MCB. The MMPA concentration in the reactor was 2%. A $Cl_2$/MMPA mole ratio of 2.5–2.8 was maintained throughout the run. The reactor hold-up time was 2 minutes, the reactor temperature was 35°–38° C. and the exiting reaction mixture was fed into a second stirred reactor. The hold-up time in this reactor was 10 minutes, the temperature was 28°–30° C. and air was passed through the stirred slurry at 150 liter/hour. On exiting the second reactor, the slurry was collected in ca. 5–8 liter batches, cooled to 5° C. and filtered to obtain the crude MIT-HCl. The cake was washed with clean MCB and the combined filtrate and washings were recycled without further treatment. The run was continued for 16 hours, after which time the reactors were still clean and scale-free. After filtration, a total of 7595 g of MIT-HCl wet cake was obtained with a 5Cl/5H ratio of 4.5. This cake contained 30% w/w of residual solvent. This represents an isolated MIT yield of 87%.

EXAMPLE 12

This example illustrates the requirement for using fresh or regenerated solvent if MIT product of high stability is to be obtained. The run here described was carried out using MCB as solvent. The concentration of feedstock MMPA in MCB was 80%.

The equipment was arranged so that the MCB filtrate, from the filtration step after removal of MIT-HCl solid cake, was transferred to the MCB tank and recycled without treatment. The size of the MCB tank was such that ca. 2.5 hours operation were required to empty it. Hence, after 2.5 hours operation, the fresh MCB was fully replaced by once-through MCB from the filtration step and, after 5 hours, the MCB used was twice-through. This method of recycle was continued for a total of 9 hours operation. The MIT-HCl solid was formulated in water as described in EP 0 300 483 (examples 1 and 2) and the stability of the formulation was examined at 50° C. For the period of the run, the following parameters were held constant: [A] REACTOR 1: MMPA feedstock addition rate—5 ml/min. MCB addition rate—67 ml/min, Cl$_2$ addition rate—2250 ml/min, HUT—1 minute, temperature 34°–35° C.; [B] REACTOR 2; N$_2$ flow rate—1000 ml/min, HUT 9 minutes, temperature 40°–43° C. The MIT-HCl cake, after filtration, was washed with 4 ml MCB/g cake. The washings were added to the MCB filtrate and recycled.

TABLE VII

| RUN TIME (hours from start) | STABILITY OF FORMULATION (days at 50° C. without decomposition) |
| --- | --- |
| 1 | 75 |
| 5 | 70 |
| 9 | 50 |

EXAMPLE 13

This example illustrates regeneration of used MCB via washing with 10% aqueous NaOH.

A sample of used MCB was examined by GLC and found to contain (wt %) 0.1% BETA, 0.16% 5Cl-MIT and 1.5% 4,5-dichloro-MIT. Present also were a large number of other materials (ca. 25) whose total weight percent contribution (estimated from their area % relative to that of the three known components) was ca. 2% of which at least 1.5% was due to two isomers of dichlorobenzene. This sample, on evaporation at 50° C./30 mm Hg/5 hours, left a residue of 6 wt %.

When the original example was washed once with an equal volume of 10% NaOH solution (90 minutes stirred contact time), once with water and once with 10% HCl solution, the GLC of the washed MCB now showed that all the BETA and 5Cl-MIT were reduced in quantity to non-detectable (<0.005 wt. %) and the amount of residual 4,5-dichloro-MIT was down to 0.01%. About 1% dichlorobenzenes were present and the other components were non-detectable. On evaporation, as described above, about 0.8% of residual material was left (95 area % due to two dichlorobenzenes).

EXAMPLE 14

This example illustrates regeneration of used MCB via treatment with silica gel (3 mm beads, Aldrich 25,562-9).

A sample of MCB (from the phase-separation step after dissolution of MIT.HCl cake in water) was examined by GLC and found to contain (wt %) 0.1% BETA, 0.1% 5H-MIT, 7.33% 5Cl-MIT and 0.4% 4,5-dichloro-MIT. Present also were the two isomers of dichlorobenzene (1.5%) and 0.5% (total) consisting of ca. 20 other components. This sample was stirred with the silica gel beads (pre-wetted with MCB) such that 4 g MCB were contacted with 2.5 g wetted beads. After two hours contact, the MCB was examined by GLC and found to contain 0.01% 5H-MIT, 2.1% 5Cl-MIT and 0.16% 4,5-dichloro-MIT. About 1% dichlorobenzenes were present and the other components were non-detectable.

EXAMPLE 15

This example illustrates the equivalence of fresh, regenerated (as in example 13) or distilled MCB as solvent for the process. These results were obtained in a demonstration plant, based on a 5 liter reactor.

The 5 liter reactor was operated with a HUT of 1.8 minutes and a temperature of 23°–26° C. was maintained. The second reactor (100 liter capacity) was used to collect all of he MIT slurry produced over a 4-hour run time. During collection, the slurry was stirred and degassed with a stream of dry air. Three runs were carried out, using (i) fresh MCB (ex. ATOCHEM), (ii) regenerated MCB (from MCB after ca. 4 recycles, treatment with NaOH as described in Example 13) and (iii) distilled MCB (from MCB after four recycles). The run parameters used for all runs were: Rate of feedstock addition (80% MMPA in MCB)—4.2 kg/hr, rate of MCB addition—160 liter/hour, rate of Cl$_2$ addition—5.1 kg/hr. The final wet cake was reslurried with its own weight of clean MCB, refiltered and formulated (see EP 0 300 483, Examples 1 and 2, but stability measured at 90° C.) to obtain a ca. 14% solution of MIT in water. The stability of this formulation was measured at 90° C.

TABLE VIII

| MCB TYPE | STABILITY OF FORMULATION (days at 90° C. without decomposition) |
| --- | --- |
| fresh (ATOCHEM) | 21 |
| regenerated | 19.5 |
| distilled | 20 |

EXAMPLE 16

This example illustrates the thermal stability of the solid MIT-HCl salt in contrast to the thermal instability of the solid MIT-free base. Solid MIT-HCl (containing 40–50% MCB) was obtained in the usual fashion by filtration of the slurry after degassing. Solid MIT-free base was obtained by slurring a sample of the MIT-HCl salt (wet with MCB), in DCM with excess sodium bicarbonate. The DCM supernatant was then evaporated under vacuum to leave a waxy solid MIT-free base, containing residual MCB.

Figure 1:
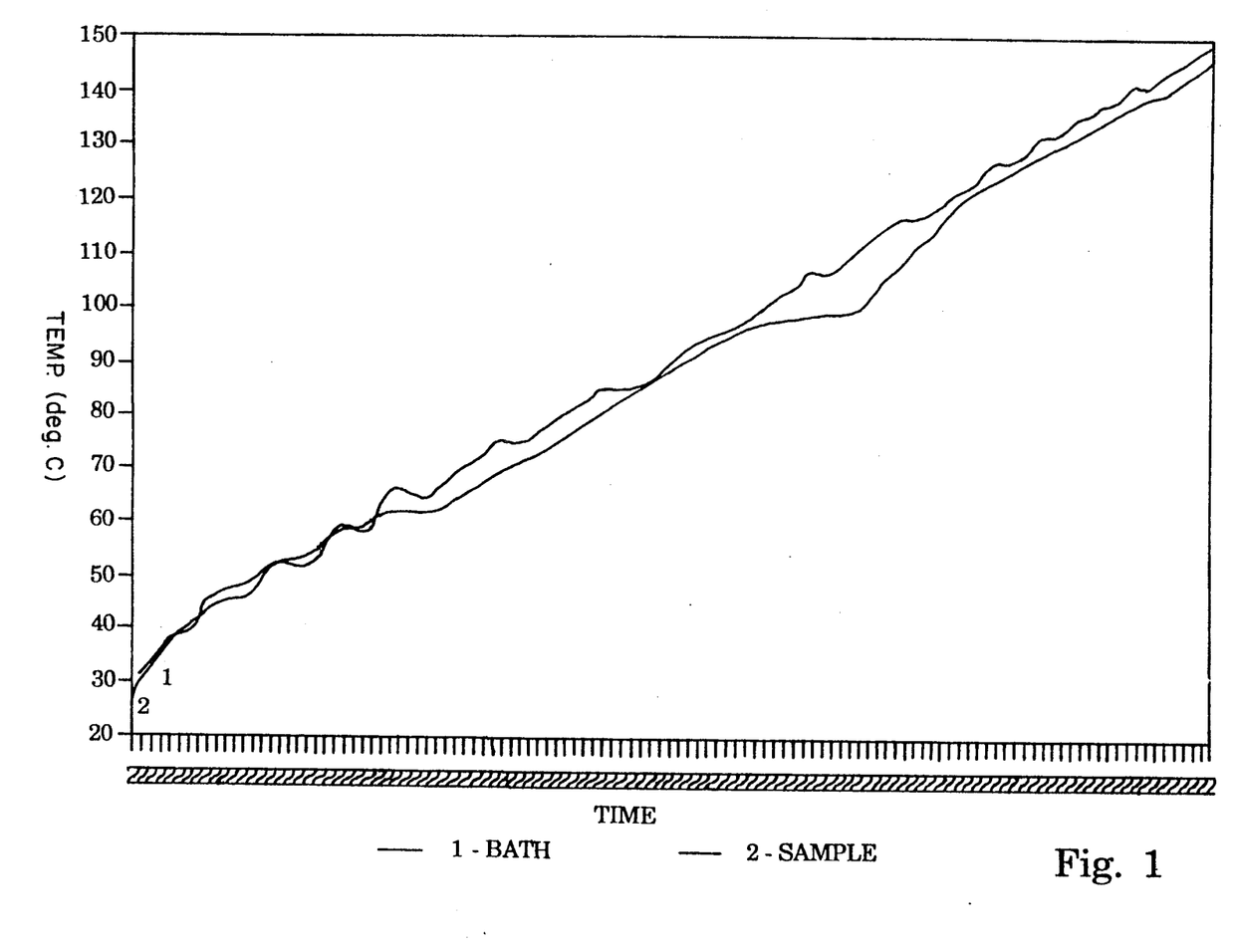
FIGS. 1 and 2 are temperature/time plots of the reaction.
Figure 2:
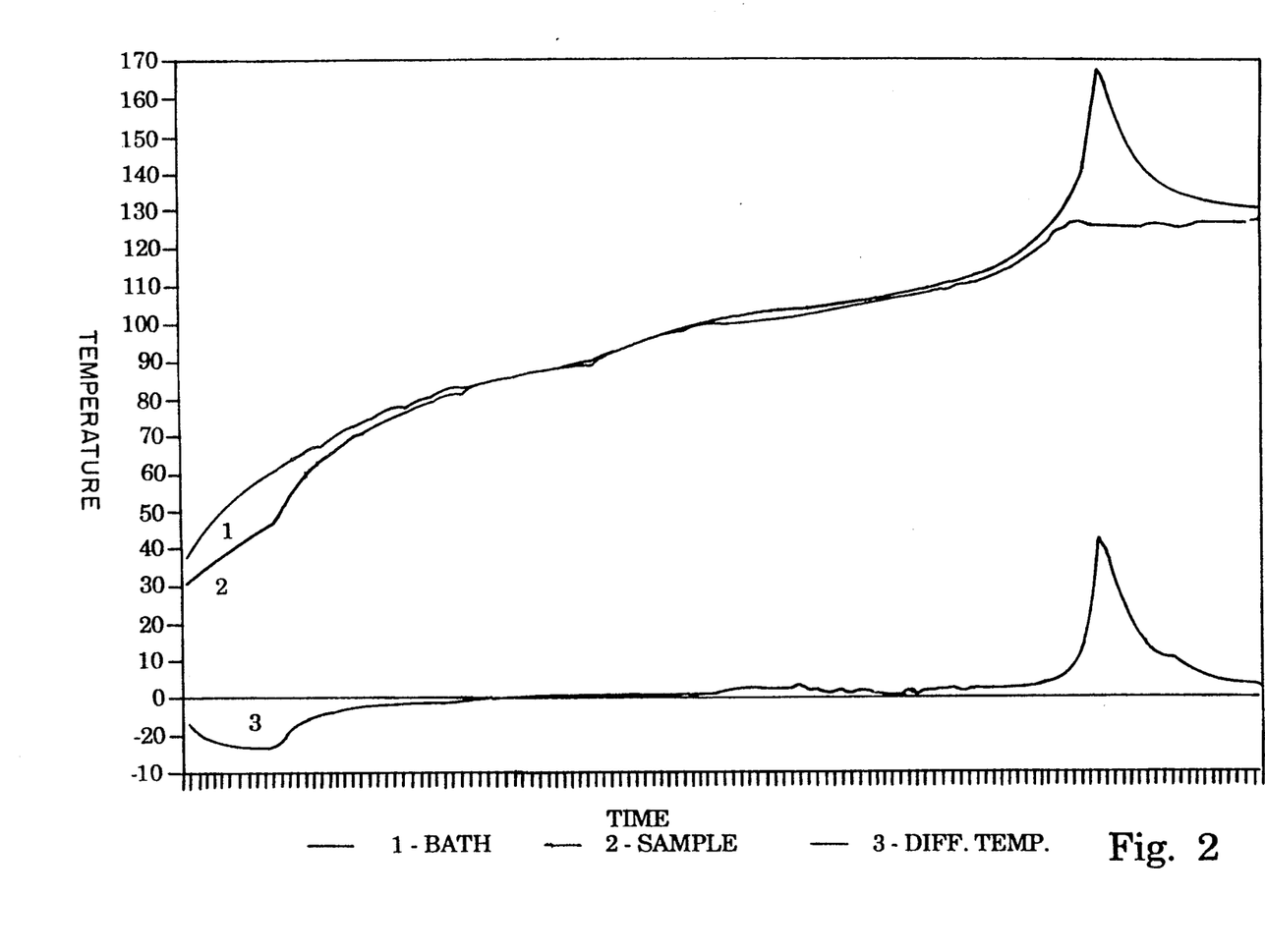

The samples, in open glass tubes, were individually heated by immersion in a thermostatted bath. The bath temperature was raised from 30°-150° C. at a constant rate by an electric element and the temperatures of bath and each sample were continuously monitored. Exothermic decomposition of the sample was indicated by a sudden rise in the sample temperature over that of the bath temperature. The attached graphs FIG. 1 and FIG. 2 show the batch and sample temperatures plotted against time for MIT-HCl salt and MIT-free base respectively. Note that the salt does not decompose exothermically but the free base does (at ca. 130° C.).

EXAMPLE 17

This example demonstrates the stability of the MIT-HCl solid on storage at temperatures below 10° C. Two samples of MIT-HCl were produced on a bench unit during November–December, 1988, analysed (quantitative GC) and stored in a refrigerator held at 4°-8° C. These samples were reanalysed in December, 1990 (24-25 months later). The results, tabulated below, clearly show the stability of the stored solid. The analysis figures refer to solvent-free solid.

TABLE IX

| Sample | Date | % BETA | % MIT.HCl | % 5Cl-MIT.HCl | % 4,5-dichloro |
|---|---|---|---|---|---|
| R31-B3 | Nov. '88 | 2.5 | 19.6 | 72.4 | 0.6 |
|  | Dec. '90 | 2.1 | 18.4 | 71.4 | 0.6 |
| R32-B4 | Dec. '88 | 1.7 | 24.3 | 74.2 | 0.3 |
|  | Dec. '90 | 1.9 | 24.6 | 72.1 | 0.3 |

EXAMPLE 18

Figure 3:
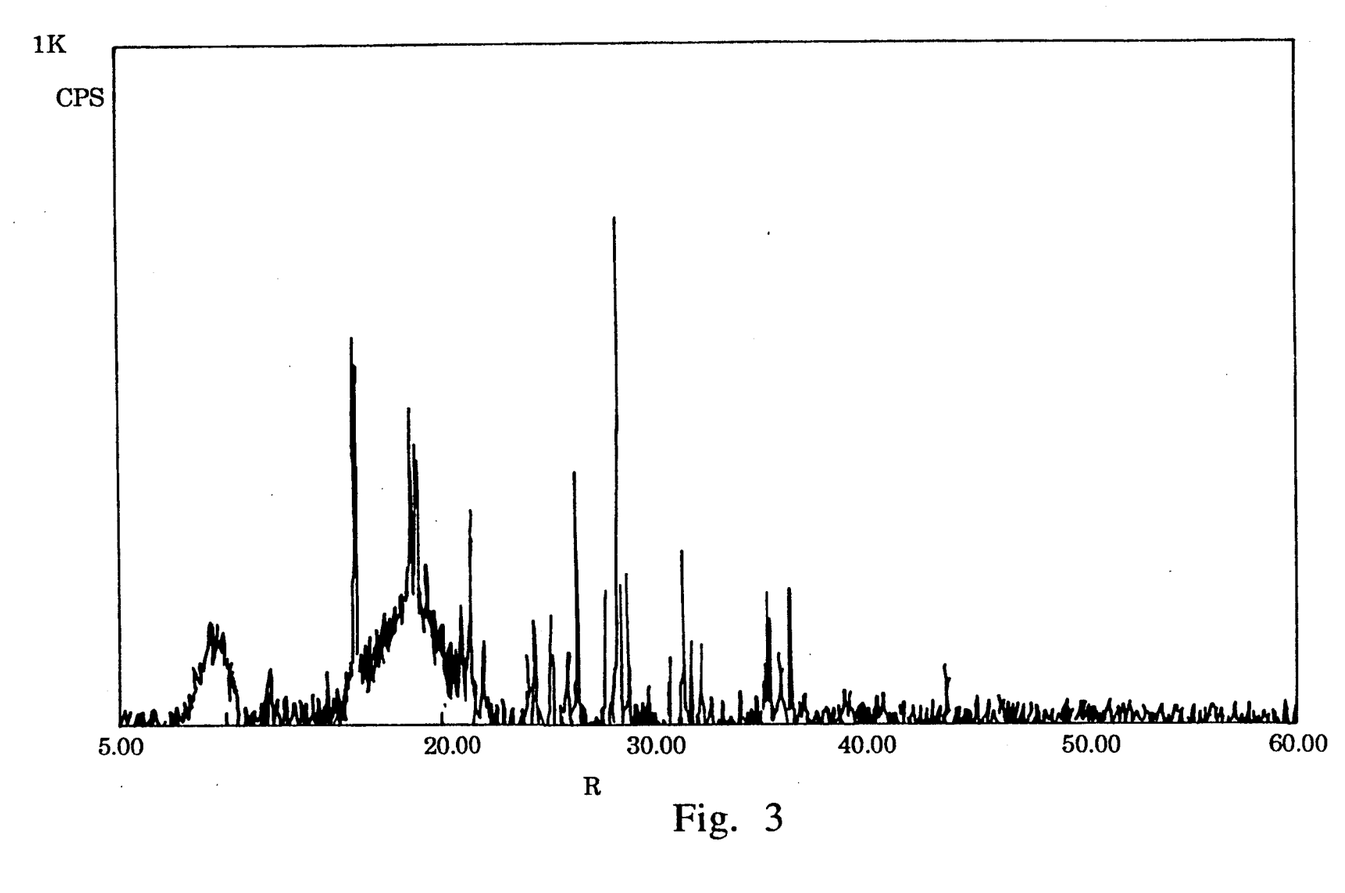
FIGS. 3–11 are x-ray diffraction patterns of samples.
Figure 4:
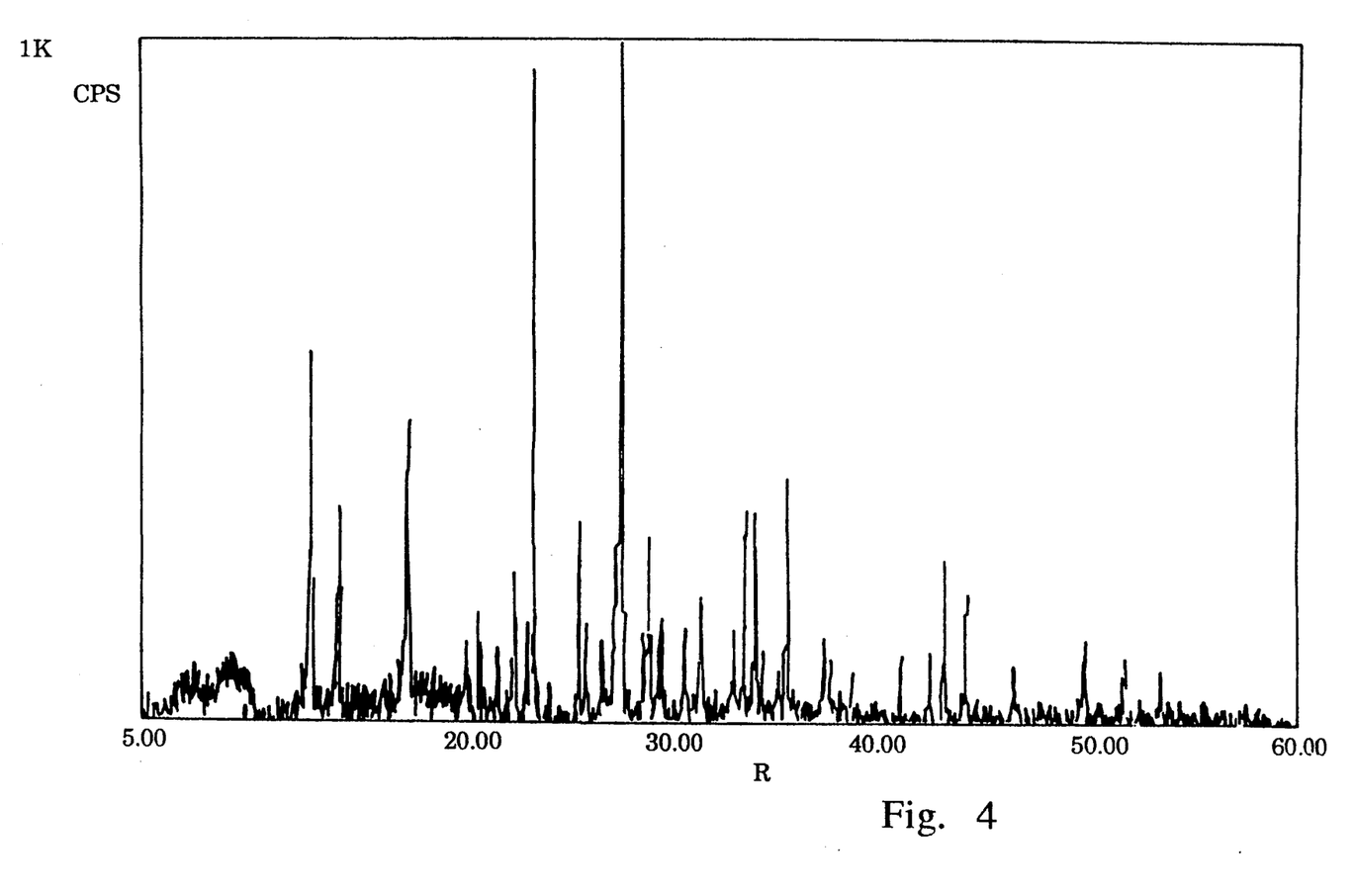

The X-ray diffraction (XRD) patterns for 5H-MIT-HCl (FIG. 3), 5Cl-MIT-HCl (FIG. 4) and several mixtures of these, as obtained in typical production runs, were measured. We found that a correlation exists between certain characteristic diffraction peaks for the two MIT components and between the GC area %s of these components.

Figure 5:
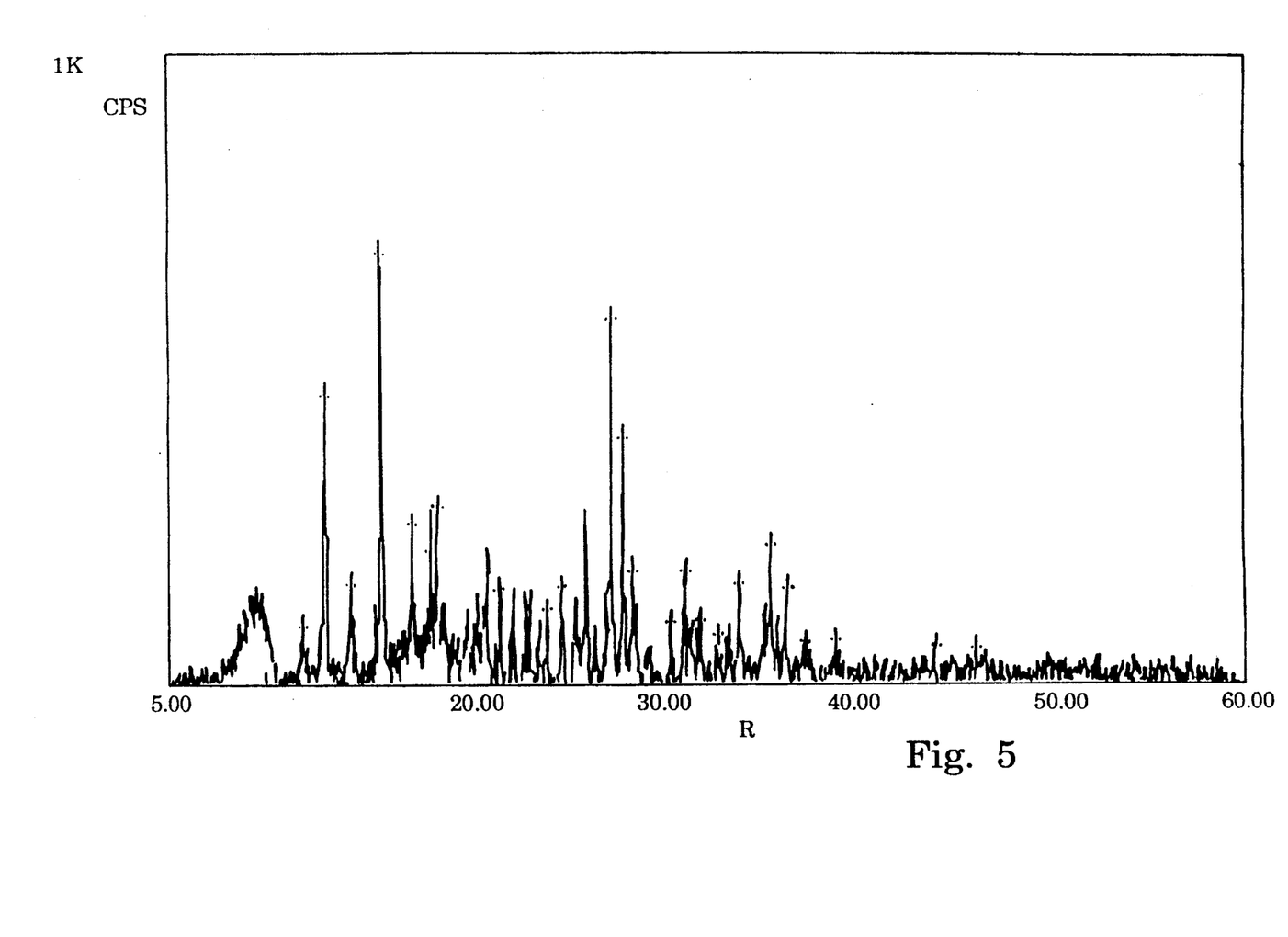
Figure 6:
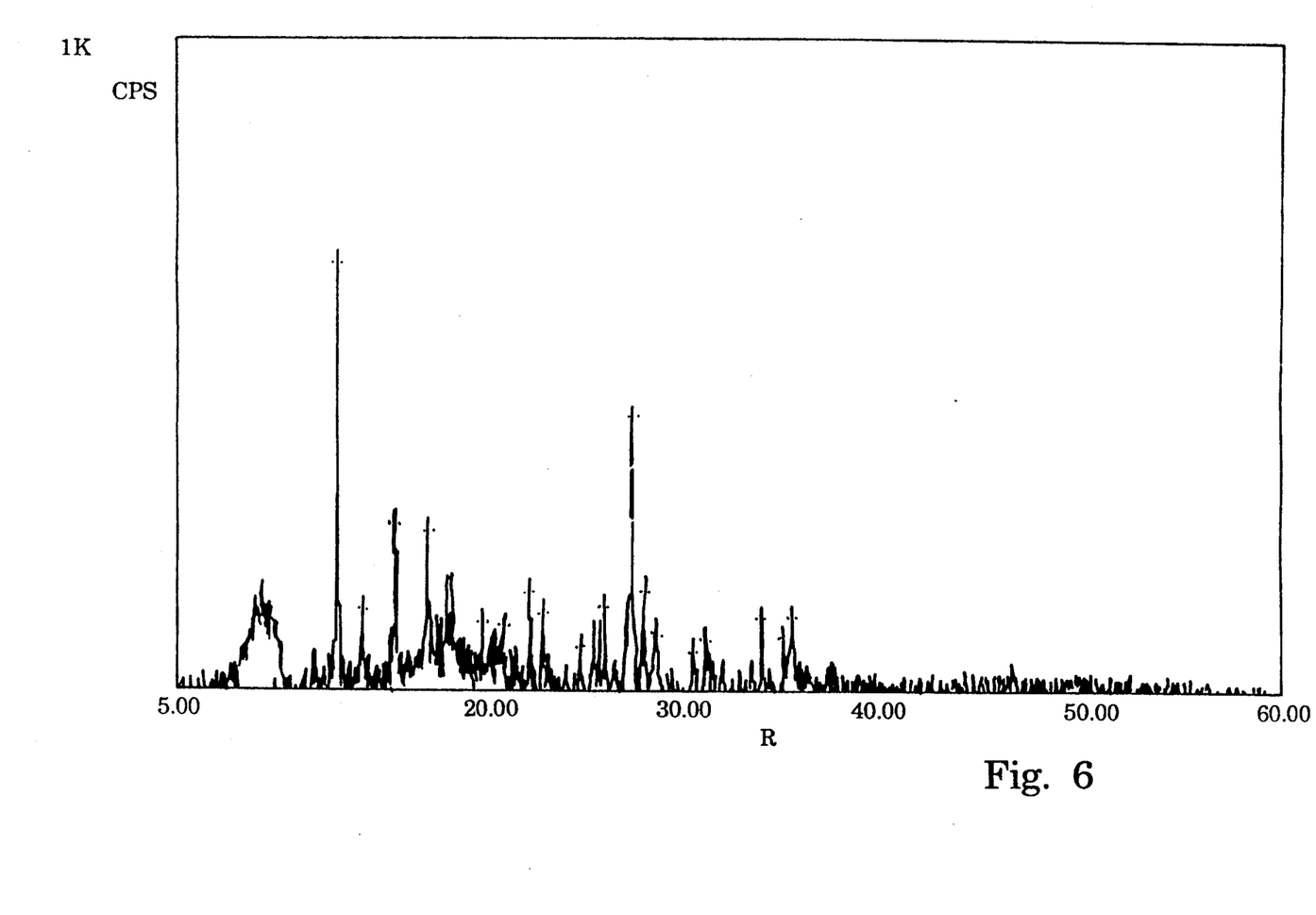
Figure 7:
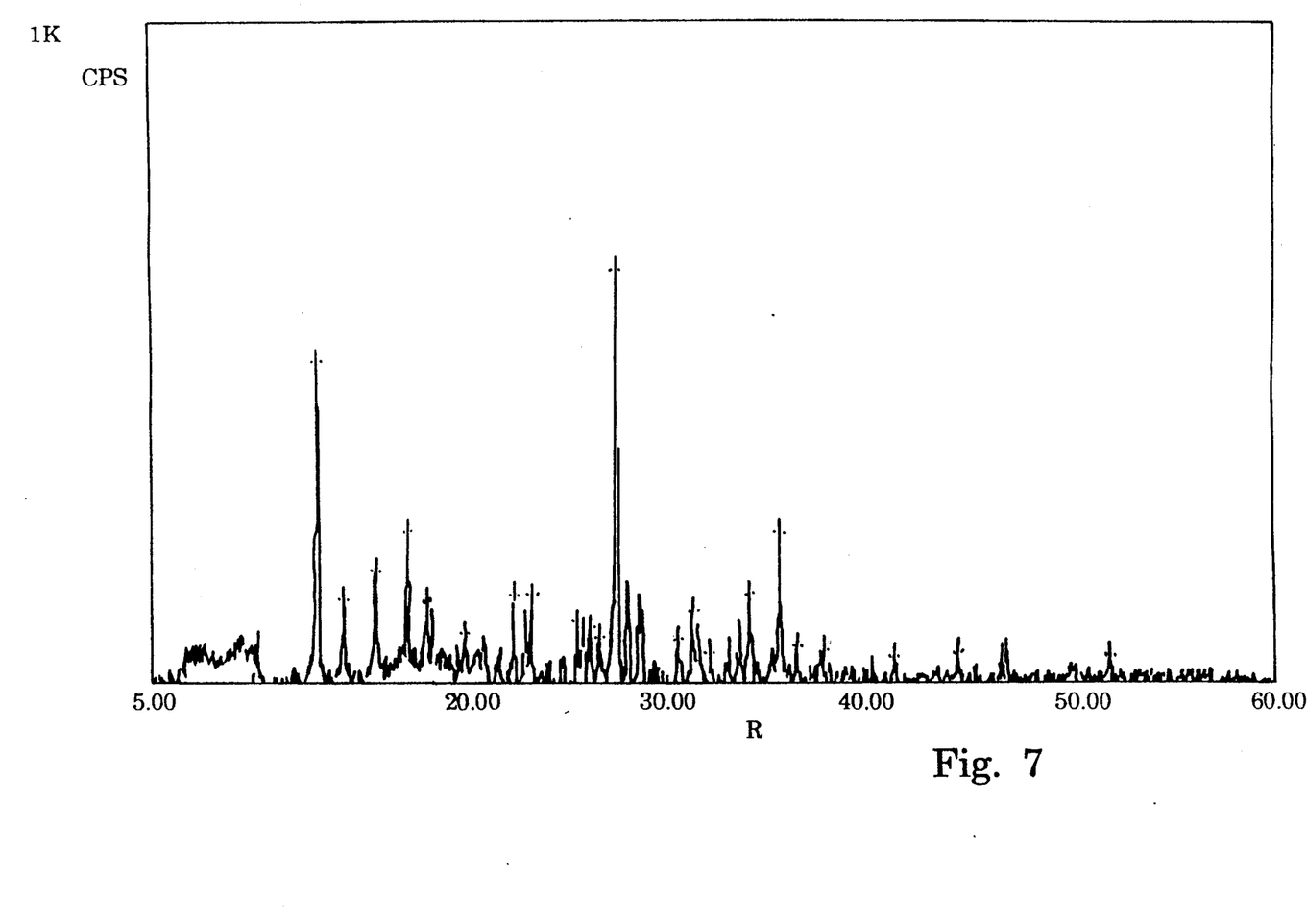
Figure 8:
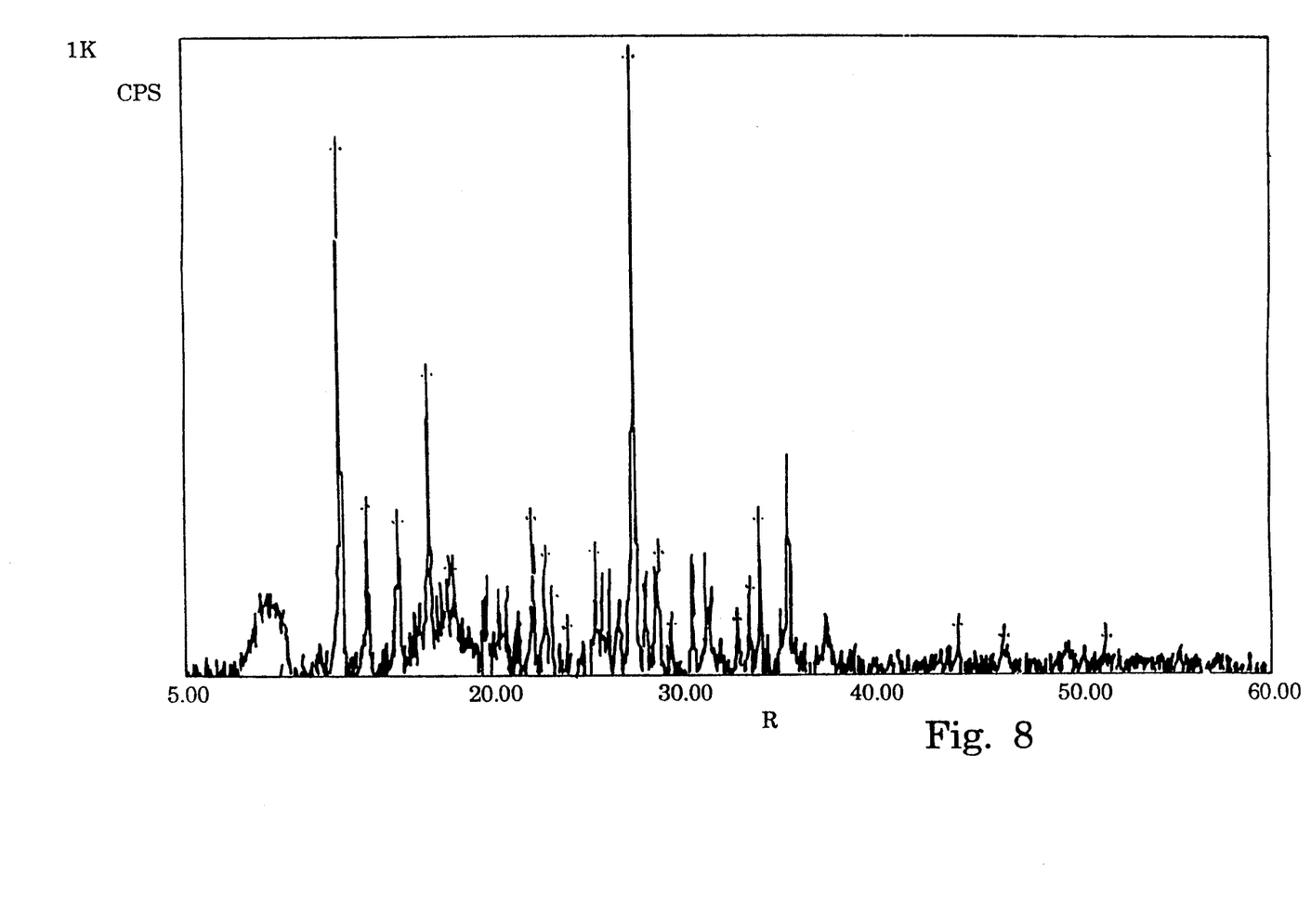
Figure 9:
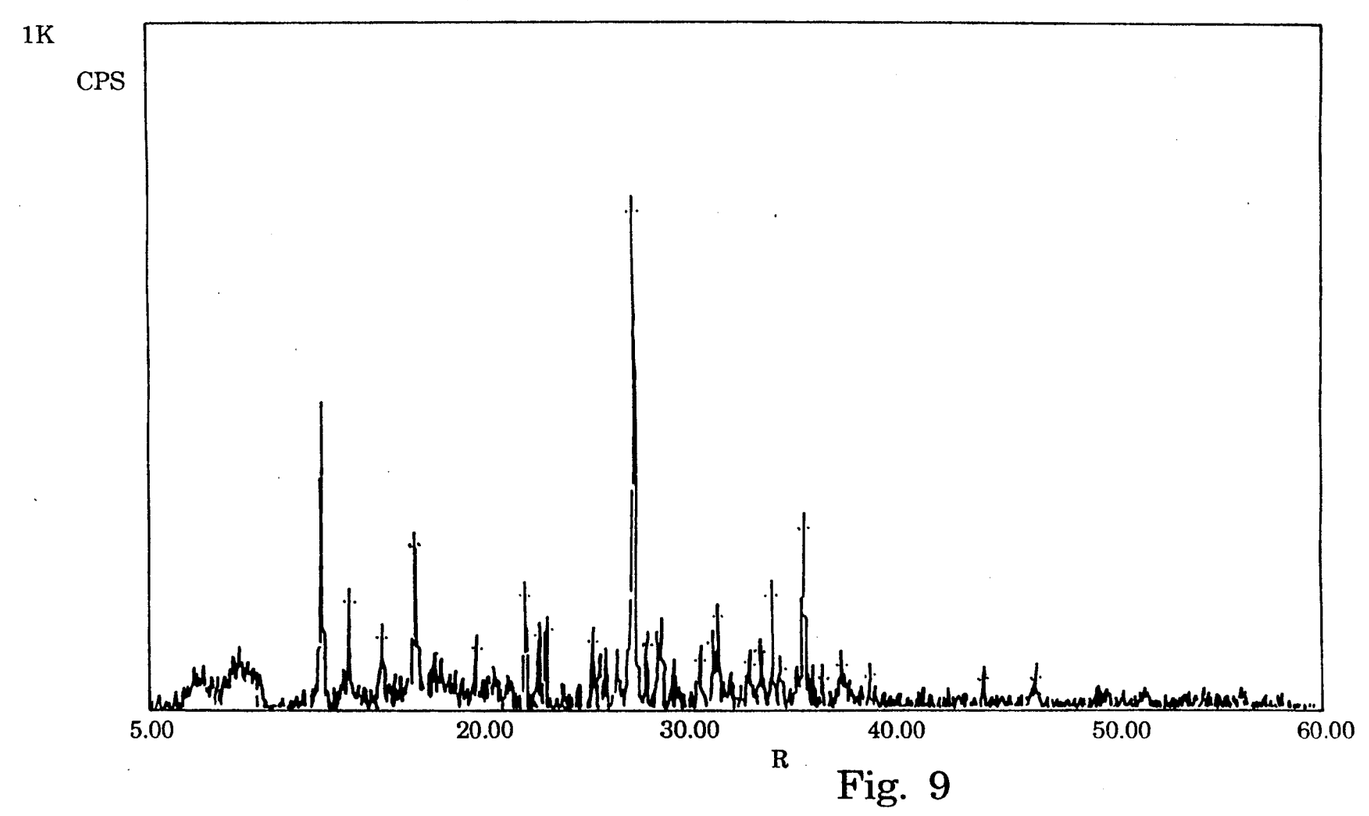
Figure 10:
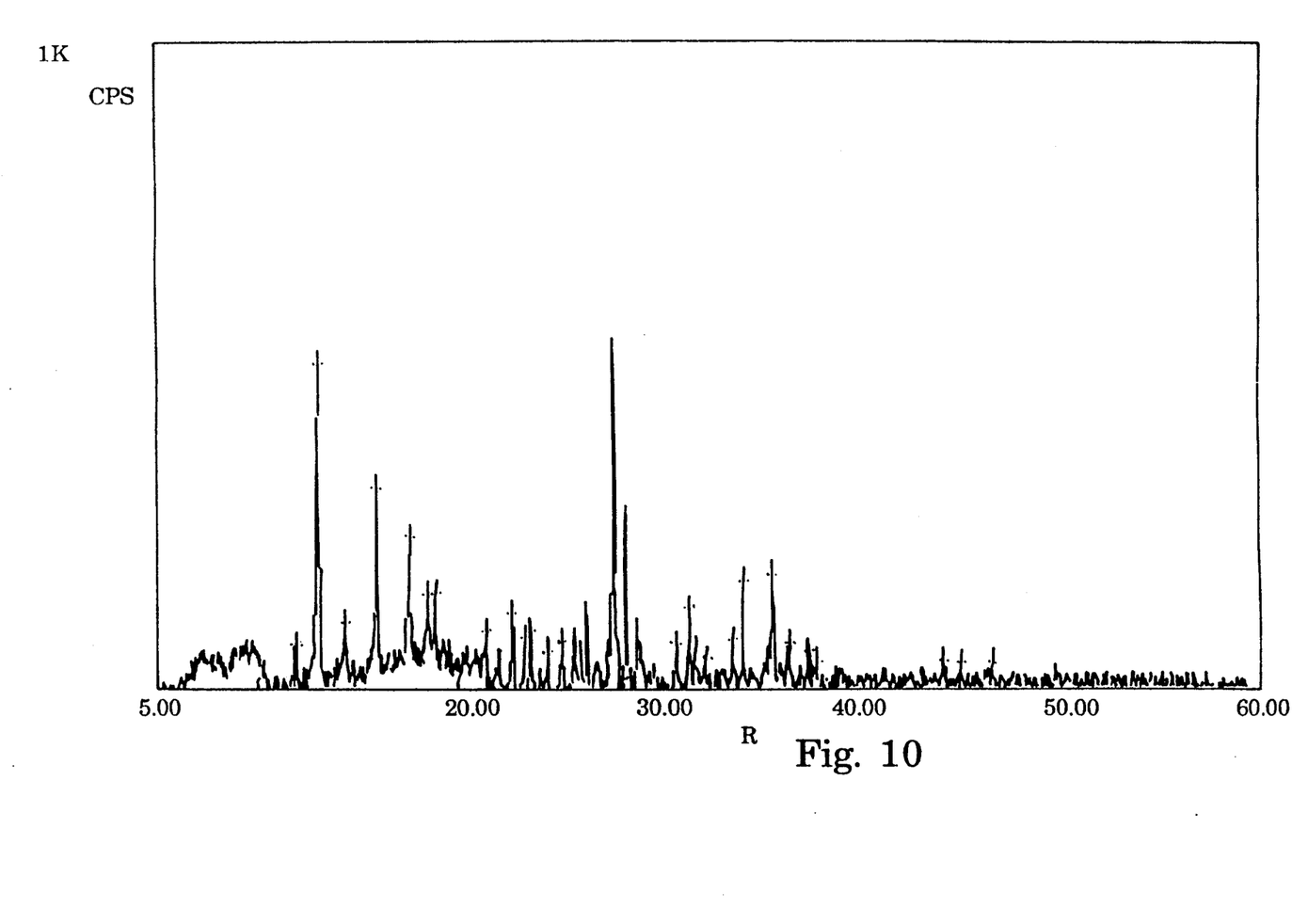
Figure 11:
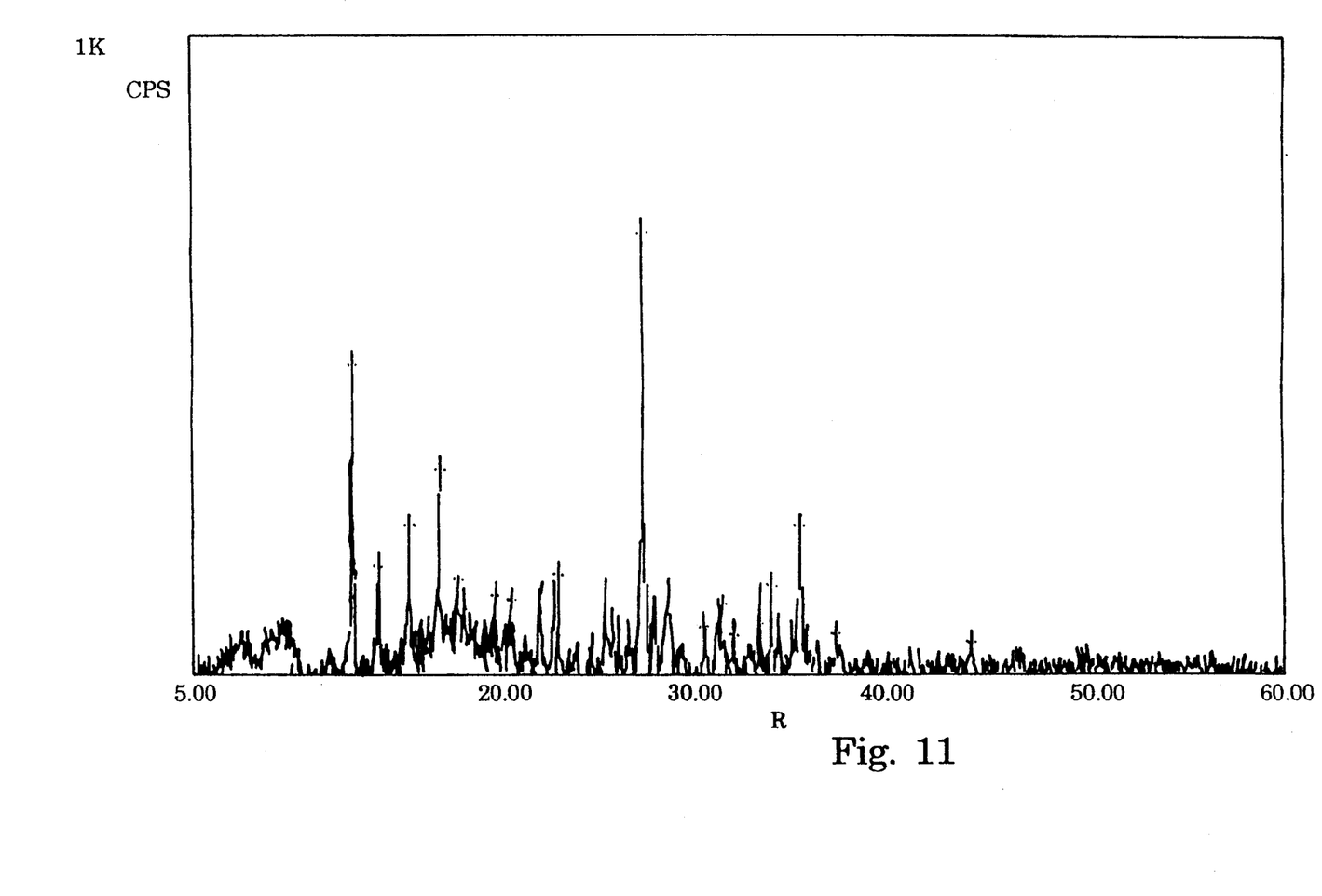

Attached are XRDs of MIT-HCl samples L13 (FIG. 5), L12 (FIG. 6), L24 (FIG. 7), L10 (FIG. 8), L19 (FIG. 9), L11 (FIG. 10) and L32 (FIG. 11), as well as those for the HCl salt of the two pure components. With respect to the pure compounds, the broad, unresolved peaks in the XRD of the 5H compound indicate that the material possesses some amorphicity, more than that exhibited by the 5Cl compound. This would be expected since the 5H salt is the least soluble in organic solvents and is rapidly precipitated without the possibility of increasing its degree of crystallinity by slow crystallization. The more soluble 5Cl salt is more crystalline (less amorphous) because it is less rapidly precipitated and crystal growth can take place. The XRDs of the MIT samples clearly show the presence of both 5H and 5Cl HCl salts. The intensity of the three strong peaks in the XRDs of the individual compounds—namely theta values of 15.97, 26.44 and 28.35 for 5H-MIT and 13.07, 23.58 and 27.75 for 5Cl-MIT—were recorded. Three sets of peak intensity ratios, representative of the relative amount of 5Cl-MIT to 5H-MIT, were calculated (i.e. 13.07/15.97, 23.58/26.44 and 27.75/26.33). These ratios are tabulated below. The average of the three XRD ratios shows an excellent correspondence (with the correlation factor of 0.7) with the GCL area % ratio.

TABLE X

| Sample | XRD Peak Intensity Ratios | | | Correlated Avg. Values | GCA % |
|---|---|---|---|---|---|
| L-13 | 0.67 | 0.52 | 1.49 | 0.6 | 0.7 |
| L-11 | 1.63 | 0.75 | 2.00 | 1.1 | 1.2 |
| L-12 | 2.54 | 0.92 | 2.65 | 1.4 | 1.3 |
| L-24 | 2.84 | 1.56 | 4.66 | 2.1 | 2.0 |
| L-32 | 2.12 | 2.18 | 6.75 | 2.6 | 2.2 |
| L-10 | 3.38 | 0.84 | 8.44 | 2.9 | 2.4 |
| L-19 | 4.14 | 1.73 | 7.67 | 3.2 | 3.2 |

While a number of embodiments of the invention have been described for the purpose of illustration, it is to be understood that the invention may be carried out by persons skilled in the art with many variations, modifications and adaptations, without departing from its spirit or from the scope of the claims.

We claim:

1. Process for the preparation of mixtures of 2-methyl-isothiazolin-3-one (5H-MIT) and 5-chloro-2-methyl-isothiazolin-3-one (5Cl-MIT), wherein the ratio of 5Cl-MIT to 5H-MIT is between 0.1 and 10.0 and wherein the yield loss due to 4,5-dichloro-MIT does not exceed 10%, which comprises chlorinating N-methyl-3-mercaptopropionamide (MMPA) with chlorine in a halogenated solvent in continuous operation.

2. Process according to claim 1, wherein the chlorination is carried out by contacting a concentrated solution of MMPA in a chlorinated solvent with gaseous chlorine or with a solution of chlorine in the same solvent.

3. Process according to claim 2, wherein the concentration of the MMPA solution is between 50 and 80%.

4. Process according to claim 1, wherein the flow of the solvent in the reactor is set as to obtain a hold-up time (HUT) in the range of 0.1 to 30 minutes.

5. Process according to claim 1, wherein the MMPA flow rate is chosen so that the concentration of MMPA in the reaction mixture is in the range of 1 to 20%.

6. Process according to claim 1, wherein the chlorine flow rate is set so as to obtain a $Cl_2$-MMPA molar ratio comprised between 1.5 and 4.0.

7. Process according to claim 1, wherein the reaction temperature is maintained in the range of 15° to 50° C.

8. Process according to claim 1, comprises carrying out the reaction in two stages, the first stage which comprises contacting the MMPA with chlorine under stirring in a first reactor, thereafter transferring the reaction mixture to a second reactor and allowing the reaction to continue, in the second stage, under stirring and under degassing for a time greater than 2 minutes.

9. Process according to claim 1, wherein the degassing is carried out to such an extent as to reduce the reduce the chlorine content of the solvent to less than 1 mole per mole of products.

10. Process according to claim 1, which comprises pre-cooling the solvent and the chlorine before their entry into the reactor and cooling the solvent and the reaction mixture during the reaction.

11. Process according to claim 1, comprising controlling the 5Cl/5H ratio of the mixture produced by controlling the concentration of the MMPA in the reactor.

12. Process according to claim 1, wherein the chlorinated solvent is selected from the group consisting of from chlorobenzene, dichloromethane, 1,2-dichloroethane, perchloroethylene and chloroform.

13. Process according to claim 8, wherein the second stage of the reaction is carried out continuously.

14. Process according to claim 8, wherein the second stage of the reaction is carried out in batch operation.

15. Process according to claim 1 which comprises regenerating and recycling the solvent.

16. Process according to claim 8, comprising filtration of the solid MIT-HCl salts from the reaction slurry.

17. Process according to claim 16, which comprises contacting with water the filter cake, wet with solvent, to extract the MIT-HCl salts therefrom, thereby releasing the solvent, containing a portion of the MIT, as a separate layer.

18. Process according to claim 17, which comprises recycling the released solvent, containing the dissolved MIT, to the second reactor.

19. Process according to claim 17, which comprises regenerating at least part of the released solvent.

20. Process according to claim 19, wherein the regeneration is carried out by a method chosen from a) distillation, b) washing with aqueous base, water and aqueous HCl, and d) passing the solvent over an absorbent.

21. Process according to claim 20, comprising carrying out the solvent regeneration by washing and further drying the solvent to reduce its water concentration to <1000 ppm.

22. A process according to claim 1, wherein the reaction temperature is maintained in the range of 20° to 40° C.

23. A process according to claim 1, wherein the reaction temperature is maintained in the range of 25° to 35° C.

24. Process according to claim 1, wherein the flow of the solvent in the reactor is set as to obtain a hold-up time (HUT) in the range of 0.5 to 7 minutes.

25. Process according to claim 1, wherein the flow of the solvent in the reactor is set as to obtain a hold-up time (HUT) in the range of 1 to 3 minutes.

26. A process according to claim 5, wherein the concentration of MMPA in the reaction mixture is in the range of from 2 to 10%.

27. A process according to claim 6, wherein the $Cl_2$-MMPA molar ratio is comprised between 2.0 and 3.2.

* * * * *